United States Patent [19]

Adamy

[11] Patent Number: 5,781,440
[45] Date of Patent: Jul. 14, 1998

[54] PROCESS AND DEVICE FOR MONITORING THE CROSS-SECTIONAL PROFILE OF A CONTINUOUSLY PRODUCED WEB OF MATERIAL

[75] Inventor: Jurgen Adamy, Bundesrepublik, Germany

[73] Assignee: Siemens Aktiengesellschaft, München, Germany

[21] Appl. No.: 652,457

[22] PCT Filed: Nov. 21, 1994

[86] PCT No.: PCT/EP94/03843

§ 371 Date: May 31, 1996

§ 102(e) Date: May 31, 1996

[87] PCT Pub. No.: WO95/15492

PCT Pub. Date: Jun. 8, 1995

[30] Foreign Application Priority Data

Dec. 2, 1993 [EP] European Pat. Off. ............ 93119465

[51] Int. Cl.$^6$ .................................................. C08F 19/00
[52] U.S. Cl. ............ 364/469.01; 162/263; 162/DIG. 10; 364/150; 364/471.03
[58] Field of Search ............ 364/468.01, 469.01–461.05, 364/473.01, 473.02, 471.01–471.03, 158, 148, 149, 176, 550, 471, 473, 551, 150, 151, 164, 165, 568; 162/198, 203, DIG. 10, 252–260, 262–263; 318/620, 561; 156/360; 34/440

[56] References Cited

U.S. PATENT DOCUMENTS

| | | | |
|---|---|---|---|
| 3,671,726 | 6/1972 | Kerr | 235/151.3 |
| 3,936,665 | 2/1976 | Donoghue | 235/151.3 |
| 3,953,713 | 4/1976 | De Light | 235/92 |
| 4,151,588 | 4/1979 | Hammer | 364/106 |
| 4,855,941 | 8/1989 | Berruyer | 364/550 |
| 4,874,467 | 10/1989 | Karlsson et al. | 162/198 |
| 4,931,982 | 6/1990 | Hayashida et al. | 364/473 |
| 5,170,357 | 12/1992 | Sasaki et al. | 364/471 |
| 5,381,341 | 1/1995 | Herrala et al. | 364/471 |

FOREIGN PATENT DOCUMENTS 0 351 260   1/1990   European Pat. Off.

OTHER PUBLICATIONS

R. Münch: "Der JETCOmmander—ein fortschrittliches System zur Fernverstellung der Stoffauflaufblende und zur Regelung des Flächengewicht-Querprofils", Wochenblatt für Papierfabrikation 7, 1992, pp. 259–265.

*Primary Examiner*—Joseph Ruggiero
*Attorney, Agent, or Firm*—Kenyon & Kenyon

[57] ABSTRACT

A predetermined number of actuators are arranged transversally to a continuously produced material web for adjusting the cross-sectional profile of the web. To determine to what degree the instantaneous cross-sectional profile can approximate a reference profile, an optimally achievable profile is determined first in a computing device on the basis of a measured profile and a mathematical model of a controlled system of a cross-sectional profile control, and the optimally achievable profile is compared with the measured profile.

10 Claims, 6 Drawing Sheets

PROCESS AND DEVICE FOR MONITORING THE CROSS-SECTIONAL PROFILE OF A CONTINUOUSLY PRODUCED WEB OF MATERIAL

FIELD OF THE INVENTION

The present invention relates to a method and a device for monitoring the cross-sectional profile of a continuously produced web of material.

BACKGROUND INFORMATION

In many processes where continuous webs of material are produced, it is of interest to provide products such as, for example, paper webs or foils with the most uniform possible characteristics; thus, these products should be homogenous and of a consistent quality. To obtain the relevant material characteristics, e.g., thickness, specific weight, or moisture content (having a numerical representation), the characteristics are measured in the longitudinal and transversal directions of the web of material and are represented as a profile in these directions. The cross-sectional profile is normally obtained broken down into a number of measured values, where the profile is average-free or is made average-free. It is desirable for the measured profile to correspond to a predefined reference profile, the reference profile is often being a zero. To achieve the desired correspondence, a predefined number of actuators, driven by a control system as a function of the system deviation between the given reference profile and the measured profile, is placed transversally to the material web.

An apparatus having a control device in which the actual cross-sectional profile control is optimized, is shown in U.S. Pat. No. 5,170,357.

It is possible that a cross-sectional profile cannot be given all desired shapes with a finite number of actuators. In particular, absolute smoothness cannot be achieved. Accordingly, it is questionable as to what extent the reference profile can be approximated by controlling the cross-sectional profile.

An article, R. Münch, "Der JETCOmmander—ein fortschrittliches System zur Fernverstellung der Stoffauflaufblende und zur Regelung des Flächengewicht-Querprofils" (The JETCOmmander—an advanced system for remote adjustment of the material winding aperture and control of the surface weight cross-sectional profile) Wockenblatt fuer Papierfabrikation 7, 1992, pp. 259–265, illustrates a process for estimating the improvement potential when a surface weight cross-sectional profile on a papermaking machine is controlled, where the variance of the measured profile is broken down into its wavelength components from which the improvement potential of the measured profile is estimated. In such a process, the accuracy of the estimate is limited since the optimum achievable profile is unknown.

In contrast, the object of the present invention is to provide a process and design means to improve the evaluation of the control devices for cross-sectional profiles of continuously produced material webs.

SUMMARY OF THE INVENTION

The present invention relates to a method and a device, wherein the optimally achievable profile is calculated in a computing device as a function of the measured profile and a mathematical model of the controlled system and made available for comparison with the measured profile for cross-sectional profile control with a control device, to whose input the system deviation between a predefined reference profile and the measured profile are supplied, and which actuates, at its output, a predefined number of actuators as a function of the system deviation to adjust the profile of the material web.

An advantage of the method and device according to the present invention consists of determining the actually desired, optimally achievable, profile first, where the profile is not constant and is dependent on the profile measurements. By comparing to the measured profile, a highly graphic evaluation tool is provided for estimating the possible profile improvement.

DETAILED DESCRIPTION

Figure 1:
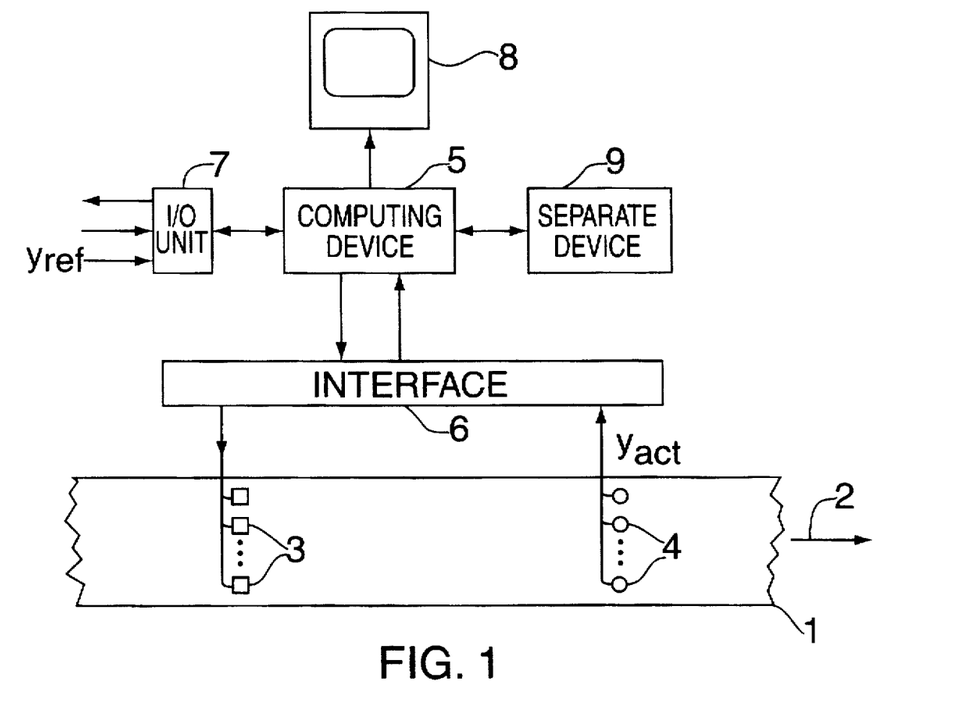
FIG. 1 shows a block diagram of a device for executing the method according to the present invention.

FIG. 1 shows a device for controlling the cross-sectional profile of a continuously produced material web 1, where the process to be controlled (obtaining a predefined cross-sectional profile) takes place in the direction of arrow 2. To adjust the cross-sectional profile of material web 1, a predefined number of n actuators 3 are arranged preferably evenly spaced over the entire width of material web 1. As shown in direction 2 of the process flow, another m number of sensors 4, which sense the cross-sectional profile of material web 1 which are broken down into m measured values, are arranged behind actuators 3. A computing device 5, consisting of a digital computer with RAM, program storage, and data storage devices, is used for controlling the cross-sectional profile of material web 1. An interface module 6 is provided between computing device 5 and the process. Computing device 5 generates control commands for actuators 3 according to the control program ran by the computing device 5 whose commands are supplied to actuators 3 through interface module 6. The control commands for actuators 3 are generated as a function of the system deviation between the actual profile $y_{act}$ measured by sensors 4 (and supplied to computing device 5 through interface module 6) and a predefined reference profile $y_{ref}$. $y_{ref}$ is supplied to computing device 5 through an input/output unit 7, through which computing device 5 communicates with the outside world. Furthermore, a display device 8 for displaying the process parameters is connected to computing device 5. Computing device 5 is also connected to a separate device 9, which is either another computing device or a program designed to be run in computing device 5 to execute the procedure according to the present invention.

Figure 2:
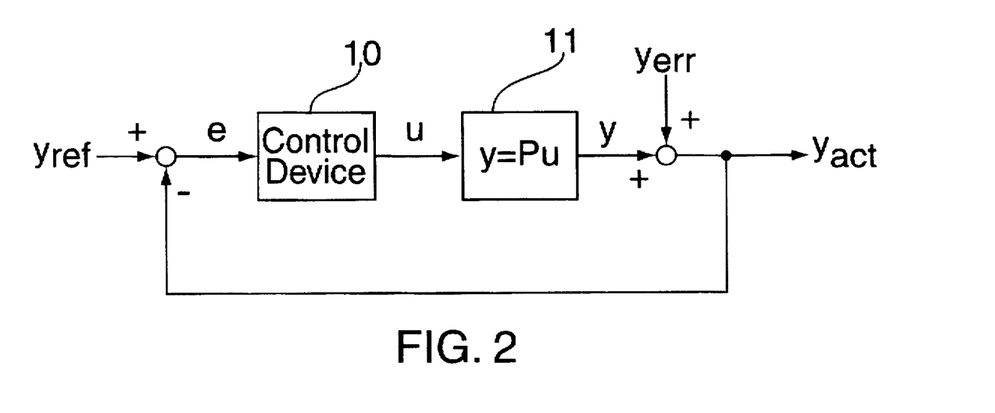
FIG. 2 shows a structure of a control circuit for controlling cross-sectional profiles as shown in FIG. 1 according to the present invention.

FIG. 2 shows a structure of the cross-sectional profile control circuit shown in FIG. 1. This control circuit consists of a control device 10 and a controlled system 11. Control device 10 is implemented as a program running in computing device 5, and controlled system 11 is formed by the process to be controlled, (e.g., the adjustment of the cross-sectional profile of material web 1). Control device 10 generates control parameters which act on the process through actuators 3 or the control profile u from the system deviation e between the reference profile $y_{ref}$ and the measured actual profile $y_{act}$. According to the characteristics of the process to be controlled, the initial profile y is formed from control profile u in the controlled system 11. The measured actual profile $y_{act}$ consists of the initial profile y and a process-specific error profile $y_{err}$. Depending on the number m of sensors 4, the actual profile $y_{act}$ reference profile $y_{ref}$ error profile $y_{err}$ initial profile y and system deviation e are formed using an m-dimensional vector with m parameters. Control profile u is represented in the form of an n-dimensional vector combining the control parameters for the n actuators 3. Assuming that the process to be controlled includes a linear characteristic, the static component shall only be discussed, (i.e., the mxn transfer matrix P formed by initial profile y from control profile u, with y=Pu).

It is possible that a cross-sectional profile y may not be given all desired shapes with a finite number n of actuators 3. To estimate the potential for improvement of the cross-sectional profile control, first the optimum achievable profile (the profile with the smallest variance $\sigma^2$ and therefore the smallest standard deviation $\sigma$) is calculated first in unit 9 for the predefined reference profile $y_{ref}$ and for a process-specific error profile $y_{err}$. Normally, in practice, variance $2\sigma$ is used as the quality criterion for the adjusted profile.

The m-dimensional profile of the system deviation is as follows:

$$e = y_{ref} - (Pu + y_{err}).$$

Accordingly, the variance is:

$$\sigma^2 = e^T e = (y_{ref} - Pu - y_{err})^T (y_{ref} - Pu - y_{err})$$

and thus the standard deviation $\sigma$ is minimized using u.
A minimum variance $\sigma^2$ is obtained when:

$$\delta\sigma^2/\delta u = -2P^T(y_{ref} - y_{err}) + 2P^T P u_{opt} = 0.$$

Accordingly, the following result is obtained:

$$u_{opt} = (P^T P)^{-1} P^T (y_{ref} - y_{err}).$$

Thus, for the optimum profile $e_{opt}$ we obtain:

$$e_{opt} = (I - (P^T P)^{-1} P^T)(y_{ref} - y_{err})$$

with the mxn unit matrix I and the pseudo-inverse $$P^0 = (P^T P)^{-1} P^T.$$

Denoting $$y_{err} = y_{act} - Pu,$$

error profile $y_{err}$ is obtained and the smallest possible system deviation achievable in the optimum case is:

$$e_{opt} = (I - P(P^T P)^{-1} P^T)(y_{ref} - y_{act}).$$

With the method and the device according to the present invention, the best possible cross-sectional profile, i.e., the profile with the smallest possible variance or standard deviation, is obtained in unit 9 for a given reference profile $y_{ref}$ directly from the measured actual profile $y_{act}$. The optimum profile $e_{opt}$ of the system deviation is supplied to display device 8 together with the instantaneous profile of the system deviation $e = y_{ref} - y_{act}$, where it is represented graphically. The direct graphic comparison between the optimum profile $e_{opt}$ and the instantaneous control error profile e makes it possible to evaluate the improvement potential still available. It can also be used for demonstrating that a profile can no longer be improved, or that a certain jaggedness in the measured profile can no longer be diminished. Of course, such a comparison between the optimum profile $e_{opt}$ and the instantaneous control error profile e can also be made automatically in unit 9 or computing device 5.

Figure 3:
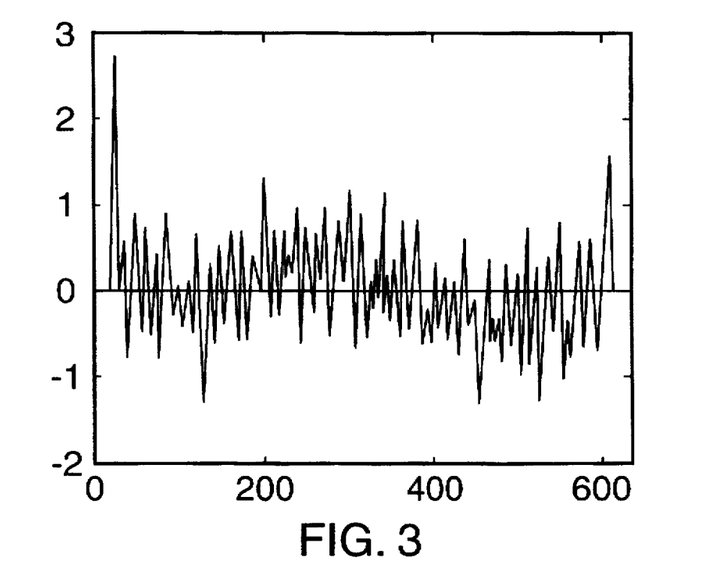
FIGS. 3–6 show possible representations of measured and corresponding optimum achievable profiles determined by the method and the device of the present invention.
Figure 4:
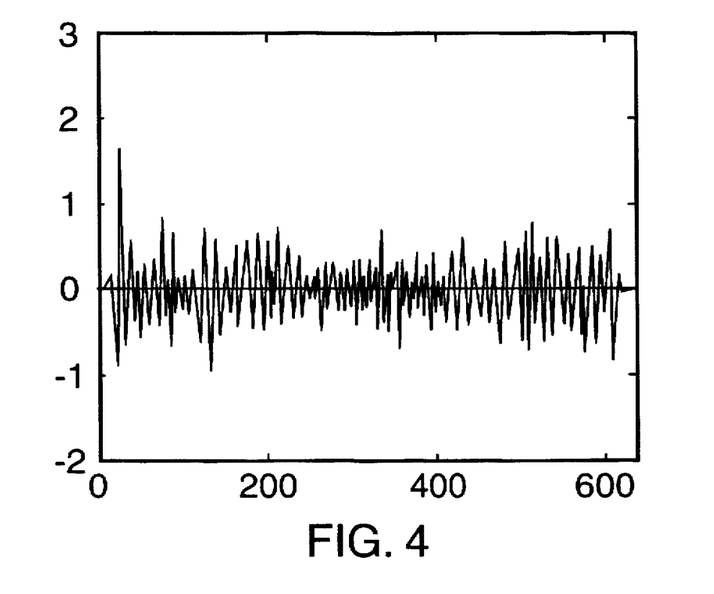
Figure 5:
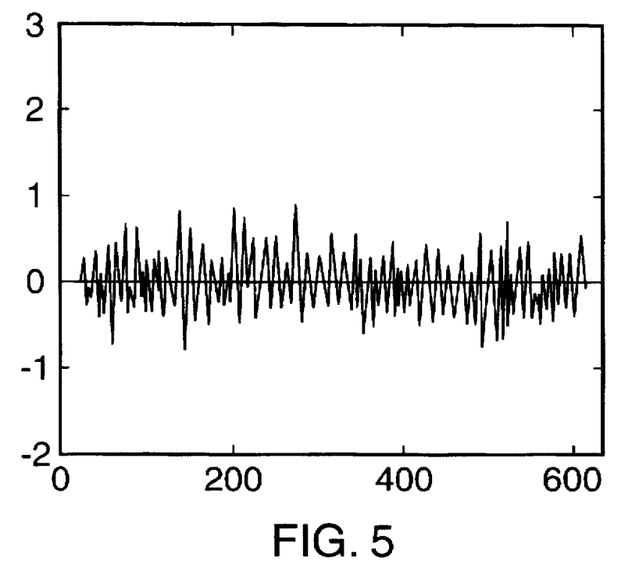
Figure 6:
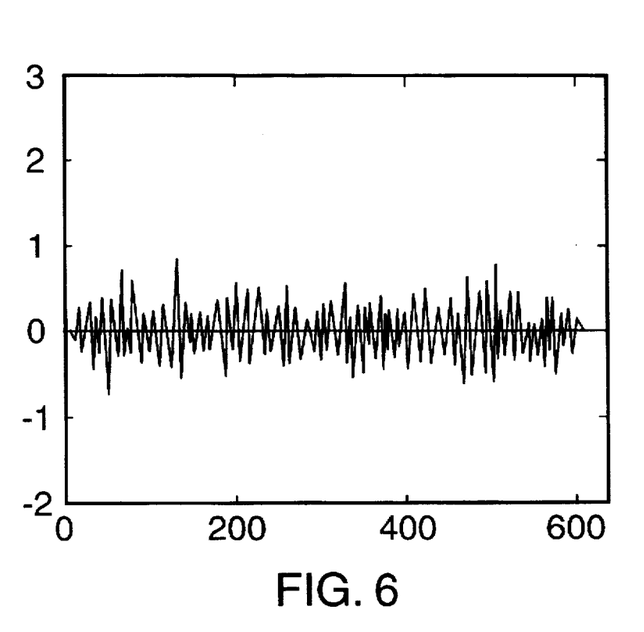

FIG. 3 shows, using an example of the cross-sectional profile control of a papermaking machine, where the surface weight cross-sectional profile is measured prior to the beginning of the control. The corresponding optimum profile calculated in unit 9 is shown in FIG. 4. FIG. 5 shows the measured cross-sectional profile after starting the cross-sectional profile control, and FIG. 6 again shows the corresponding optimum profile. The diagrams are plotted in g/m² against measured parameters. A comparison of FIGS. 3 and 4 shows that prior to starting the cross-sectional profile control, there is still an improvement potential of 58%, while (as shown by a comparison of FIGS. 5 and 6) the improvement potential dropped to 14% after starting the control; this means that the actual profile corresponds to optimum achievable profile to a degree of 86%.

In principle, profile components with a lower frequency (components with a considerably greater wavelength than the distance between two adjacent actuators 3) may be properly adjusted, while higher-frequency components are adjusted poorly or not at all. To obtain information regarding to what extent the individual spectral components of the cross-sectional profile can be improved through control in the optimum case, the Fourier transforms E and $E_{opt}$ of the measured profiles of the system deviation e and the optimum profile $e_{opt}$ are determined in unit 9, using a transformation matrix T with the elements $$t_{k,i} = \exp(-j2\pi k i/m), \text{ where } i,k=0,1,\ldots,m-1;$$

$$E = Te$$

$$E_{opt} = Te_{opt} = T(I - P(P^T P)^{-1} P^T) T^{-1} E.$$

Figure 7:
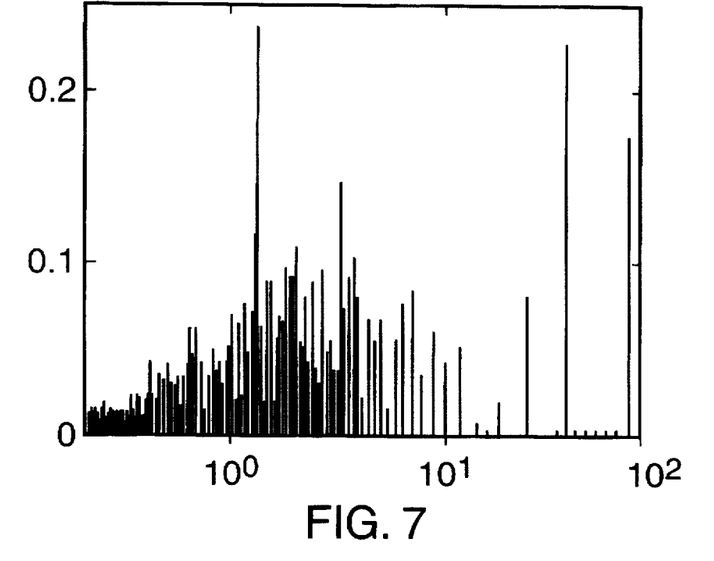
FIGS. 7–10 show the Fourier spectra of the profiles as illustrated in FIGS. 3–6.
Figure 8:
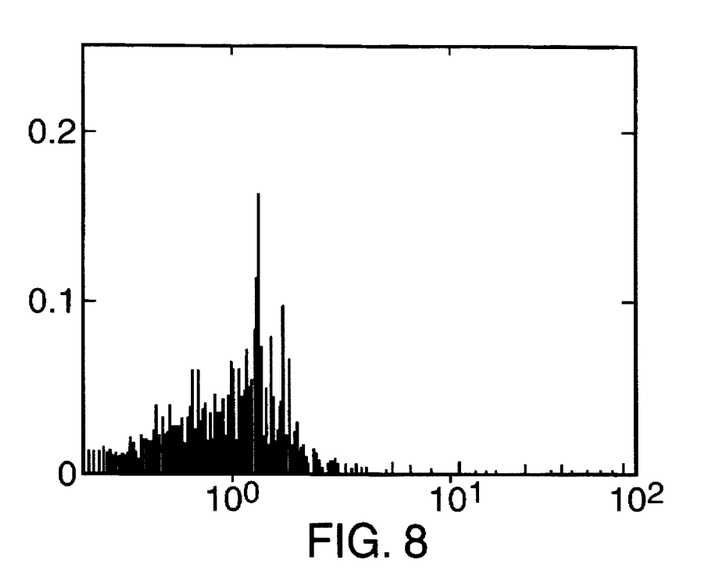
Figure 9:
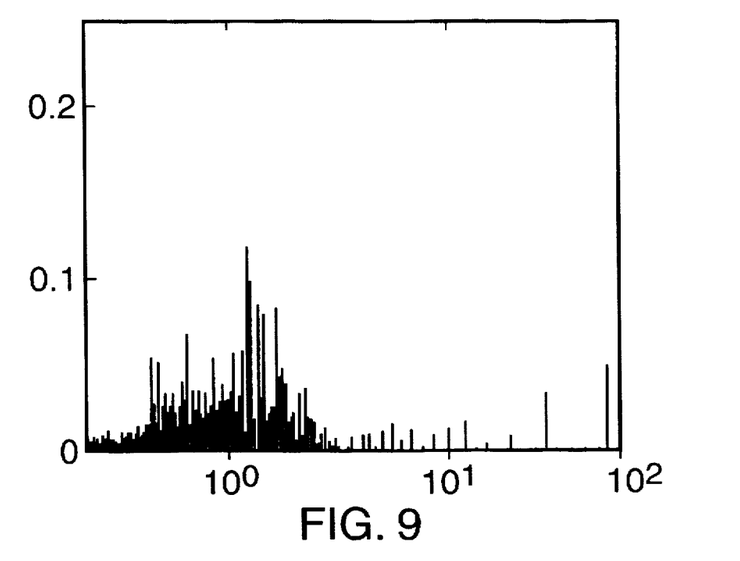
Figure 10:
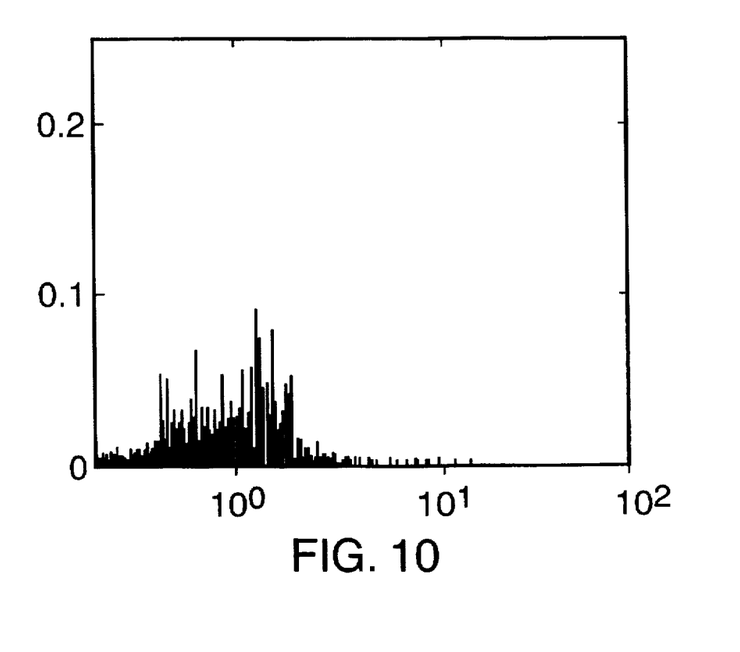

The improvement potential of the cross-sectional profile is determined using the profile spectra E and $E_{opt}$ in the same manner, as was explained above for profiles e and $e_{opt}$. FIGS. 7 through 10 illustrate such improvement using a spectra corresponding to the profiles of FIGS. 3–6. In FIGS. 3–6, the amplitudes $|E_k|$ of the individual spectral components $E_k$ are plotted against their wavelengths $$\lambda_k = m/k,$$

where the wavelengths $\eta_k$ of the individual spectral components $E_k$ are plotted as multiples of a distance between actuators. In particular, FIG. 7 shows spectrum E of the measured profile e prior to control, FIG. 8 shows spectrum $E_{opt}$ of the corresponding optimum profile $e_{opt}$. FIG. 9 shows spectrum E of the measured adjusted profile e, and FIG. 10 shows spectrum $E_{opt}$ of the corresponding optimum profile $e_{opt}$. As can be seen from FIGS. 7 through 10, the greatest improvement in the profile is achieved in the long-wavelength area.

Figure 11:
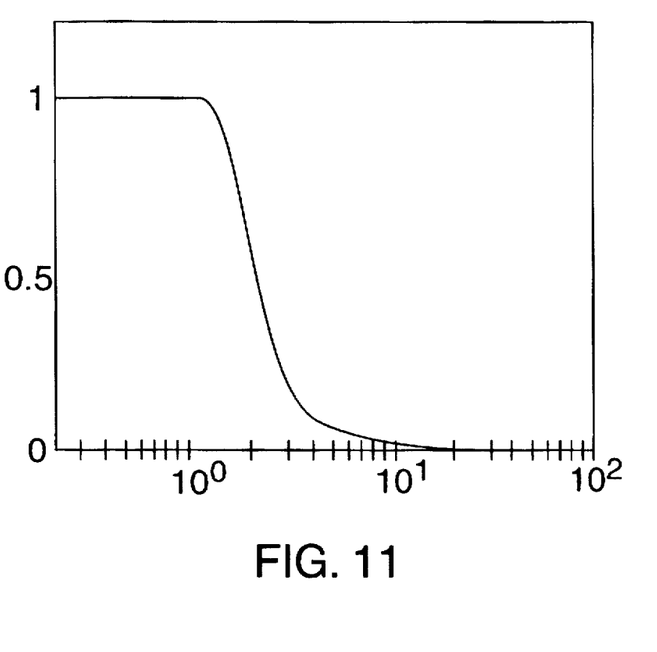
FIG. 11 shows a limit curve illustrating an optimum profile which may be obtained in the worst-case scenario according to the present invention.

As illustrated above, for each error profile $y_{err}$ or measure profile $y_{act}$ there is a corresponding special optimum profile $e_{opt}$. Each of the optimum profiles $e_{opt}$ also includes an individual spectral distribution $E_{opt}$ from which it can be seen how large are amplitudes $|E_{opt,k}|$ of the individual wavelengths $\eta_k$. Different spectral distributions $E_{opt}$ of the optimum profiles usually result in different amplitude values $|E_{opt,k}|$. One of the important parameters is the highest possible value of $|E_{opt,k}|$, e.g., its upper limit $\eta_k$. This value illustrates how bad the optimum solution for wavelength $\lambda_k$ can be in the worst case or how good it must be as a minimum. The limit $\eta_k$ shows the minimum factor by which the amplitude $|E_k|$ of an error in the wavelength $\lambda_k$ can be reduced. The limit $\eta_k$ is calculated in unit 9, accordingly:

$$\eta_k = \max_{\|E\|_2=1} |E_{opt,k}| = (1-1/m\|P(P^TP)^{-1}P^T t_k\|_2^2)^{1/2},$$

where $t_k$ denotes the kth column vector of transformation matrix T. The limit values $\eta_k$ together form the limit curve $$\eta^T = (\eta_0, \eta_1, \ldots, \eta_{m-1}),$$

which is not dependent on the individual profiles, but only on characteristic P of the controlled system 11. If characteristic P is constant, the limit curve $\eta$ can be determined only once. On the other hand, if P varies, for example, as a function of the process status, the limit curve $\eta$ must, in general, be determined again. FIG. 11 shows an example of limit curve q as a function of the wavelengths $\lambda_k$, which are shown as multiples of the distance between actuators. It can be clearly seen that hardly any improvement can be achieved for wavelengths $\lambda_k$ smaller than twice the distance between actuators.

I claim:

1. A method for monitoring a cross-sectional profile of a material web continuously produced with a controlled system characterized by a model, the method comprising the steps of:

obtaining a measured profile of the material web;

determining a control deviation between a predetermined reference profile and the measured profile;

actuating at least one actuator as a function of the control deviation for adjusting the cross-sectional profile of the material web;

calculating an optimally achievable profile as a function of the measured profile using the model of the controlled system; and comparing the optimally achievable profile and the measured profile.

2. The method according to claim 1, wherein the step of calculating the optimally achievable profile includes calculating a minimum achievable system deviation $e_{opt}$ so that:

$$e_{opt} = (I - P(P^TP)^{-1}P^T)(y_{ref} - y_{act}), \text{ wherein:}$$

$y_{ref}$ represents the predetermined reference profile, $y_{act}$ represents the measured profile, P is a transfer matrix of the controlled system for determining the cross-sectional profile y of the material web from control parameters u of the actuators, so that y=Pu, $P^T$ is a transposed matrix of the matrix P, and I is a unit matrix.

3. The method according to claim 1, wherein the step of calculating the optimally achievable profile includes calculating a Fourier transform $E_{opt}$ of a minimum achievable system deviation so that:

$E_{opt} = T[I - P(P^TP)^{-1}P^T]T^{-1}E$, wherein:

P is a transfer matrix of the controlled system for determining the cross-sectional profile y of the material web from control parameters u of the actuators, so that y=Pu, $P^T$ is a transposed matrix of the matrix P, I is a unit matrix, and T is a transformation matrix for a Fourier transformation.

4. The method according to claim 3, further comprising the step of:

calculating limit values $\eta_k$ so that:

$$\eta_k = (1-1/m\|P(P^TP)^{-1}P^T t_k\|_2^2)^{1/2},$$

the limit values $\eta_k$ representing a spectral limit curve $\eta^T$ so that:

$$\eta^T = (\eta_0, \eta_1, \ldots, \eta_{m-1}),$$

wherein the spectral limit curve $\eta^T$ provides the largest amplitudes of a Fourier spectrum of the minimum achievable control deviation independently of the control deviation, and wherein m is a number of column vectors and $t_k$ is a kth column vector of the transformation matrix T.

5. The method according to claim 1 including the step of displaying at least one of the measured profile, the optimum achievable profile, a Fourier transform of the measured profile and a Fourier transform of the optimum achievable profile.

6. A device for monitoring a cross-sectional profile of a continuously produced material web continuously produced with a controlled system characterized by a model, comprising:

a measuring device for obtaining a measured profile of the material web;

means for determining a control deviation between a predetermined reference profile and the measured profile;

a control device including a control input and an output, the control input receiving the control deviation;

at least one actuator coupled to the output of the control device, the control device controlling the at least one actuator as a function of the control deviation for adjusting the cross-sectional profile of the material web;

a computing device for calculating an optimum achievable profile as a function of the measured profile using the model of the controlled system; and means for comparing the optimally achievable profile and the measured profile.

7. The device according to claim 6, wherein the computing device calculates the optimally achievable profile by calculating a minimum achievable system deviation $e_{opt}$ so that:

$$e_{opt} = (I - P(P^TP)^{-1}P^T)(y_{ref} - y_{act}), \text{ wherein:}$$

$y_{ref}$ represents the predetermined reference profile, $y_{act}$ represents the measured profile, P is a transfer matrix of the controlled system for determining the cross-sectional profile y of the material web from control parameters u of the actuators, so that y=Pu, $P^T$ is a transposed matrix of the matrix P, and I is a unit matrix.

8. The system according to claim 6, wherein the computing device calculates the optimally achievable profile by calculating a Fourier transform $E_{opt}$ of a minimum achievable system deviation so that:

$E_{opt} = T[I - P(P^TP)^{-1}P^T]T^{-1}E$, wherein:

P is a transfer matrix of the controlled system for determining the cross-sectional profile y of the material web from control parameters u of the actuators, so that y=Pu, $P^T$ is a transposed matrix of the matrix P, I is a unit matrix, and T is a transformation matrix for a Fourier transformation.

9. The system according to claim 8, wherein the computing device calculates limit values $\eta_k$ so that:

$$\eta_k = (1 - 1/m \|P(P^TP)^{-1}P^T t_k\|_2^2)^{1/2},$$

the limit values $\eta_k$ representing a spectral limit curve $\eta^T$ so that:

$$\eta^T = (\eta_0, \eta_1, \ldots, \eta_{m-1}),$$

wherein the spectral limit curve $\eta^T$ provides the largest amplitudes of a Fourier spectrum of the minimum achievable control deviation independently of the control deviation, and wherein m is a number of column vectors and $t_k$ is a kth column vector of the transformation matrix T.

10. The device according to claim 6, further comprising:

a displaying device for displaying at least one of the measured profile, the optimum achievable profile, a Fourier transform of the measured profile and a Fourier transform of the optimum achievable profile.

\* \* \* \* \*